United States Patent [19]

Douglas et al.

[11] 4,418,209

[45] Nov. 29, 1983

[54] AMIDINOTHIOUREAS

[75] Inventors: George H. Douglas, Malvern, Pa.;
Julius Diamond, Morris Plains, N.J.;
William L. Studt, Harleysville; Stuart
A. Dodson, Lansdale, both of Pa.

[73] Assignee: William H. Rorer, Inc., Fort Washington, Pa.

[21] Appl. No.: 333,169

[22] Filed: Dec. 21, 1981

Related U.S. Application Data

[63] Continuation of Ser. No. 140,135, Apr. 14, 1980, abandoned.

[51] Int. Cl.$^3$ ..................... C07C 157/09; A61K 31/17
[52] U.S. Cl. ................................. 564/27; 260/465 D;
424/322; 560/34; 564/47; 564/48; 564/49;
564/50; 564/52; 564/53; 564/54; 544/160;
544/390; 544/402
[58] Field of Search ....................... 564/47, 48, 49, 50,
564/52, 53, 54, 27; 424/322; 260/465 D; 560/34

[56] References Cited

U.S. PATENT DOCUMENTS

| | | | |
|---|---|---|---|
| 3,320,229 | 5/1967 | Szabo et al. | 260/552 R |
| 4,025,652 | 5/1977 | Diamond et al. | 424/322 |
| 4,060,635 | 11/1977 | Diamond et al. | 424/322 |
| 4,088,785 | 5/1978 | Diamond et al. | 424/322 |
| 4,117,165 | 9/1978 | Diamond et al. | 424/322 |
| 4,150,154 | 4/1979 | Diamond et al. | 424/322 |

OTHER PUBLICATIONS

Ueda et al., *Chem. Pharm. Bull.* (1971), vol. 19, pp. 1990–1999.
Conant et al., "The Chemistry of Organic Compounds", 4th Ed. (1952), p. 335, Publ. MacMillan Co.
Curd et al., *J. Chem. Soc.* (1949), pp. 1732–1745.

*Primary Examiner*—Thomas A. Waltz
*Attorney, Agent, or Firm*—James A. Nicholson; Alexis Barron; Martin F. Savitzky

[57] ABSTRACT

This invention describes a new class of 1-amidino-3-phenylthiourea and N'-phenylamidinothiourea compounds wherein the phenyl group is ortho substituted, and processes for their preparation. The phenylamidinothiourea compounds may be incorporated into pharmaceutical preparations which are useful for producing anti-ulcerogenic, antisecretory, antispasmodic, antihypertensive, anti-arrhythmic, anesthetic, antidiarrheal and antiparasitic action.

9 Claims, No Drawings

AMIDINOTHIOUREAS

This application is a continuation of copending application Ser. No. 140,135, filed Apr. 14, 1980, now abandoned.

BACKGROUND OF THE INVENTION

The pharmaceutical compositions which have been used as gastric antisecretory and antispasmodic agents have been such as atropine, homatropine, propantheline bromide, dicylomine hydrochloride, and other compounds which are structurally dissimilar to the amidinoureas. Due to the anticholinergic properties of these compounds, they are known to produce undesirable side effects such as mydriasis, xerostomia, cyclopegia, and other unwanted effects.

The narcotic analgesics remain the drugs of choice for treatment of diarrhea and dysentery. This group of drugs, however, has serious disadvantages. They possess the narcotic properties of producing sleep as well as analgesia. They also have physical and psychological dependence liabilities. Morphine and codeine remain two outstanding examples of this group.

In 1957 a meperidine derivative, diphenoxylate, was introduced into the therapeutic regimen of diarrhea control. This agent possesses morphine-like as well as anticholinergic properties, both of which may be responsible for its antidiarrheal actions. Diphenoxylate, because of its narcotic properties, is capable of supporting morphine physical dependence in the monkey. Overdoses in children can lead to symptoms and fatalities that are characteristic of the narcotics, e.g., respiratory depression and reversal of morbidity with nalorphine.

Since pharmaceutical compositions other than those containing the phenylamidinoureas which have been useful in the treatment of ulcers, diarrhea, dysentery and spasms unfortunately exhibit undesirable side effects, it is desirable to find classes of compounds with minimal side effects.

Recently, a new class of phenylamidinoureas and their uses as antisecretory, antispasmodic, anti-ulcerogenic, anesthetic and antidiarrheal agents have been reported in Arzneimittel Forschung (Drug Research) 28(11), 1433–1480 (1978), and U.S. Pat. Nos. 4,058,557, 4,060,635, 4,088,785, 4,115,564, 4,117,165, 4,147,804, 4,150,154, 4,169,155 and 4,178,387. Their use in the treatment of dysmenorrhea has also been reported in copending application Ser. No. 26,281, as well as their use in the treatment of hypertension in copending application Ser. No. 26,161. Additionally, the phenylamidinoureas are known to be effective agents against protozoal infections.

Parasitic protozoal infections are difficult to eradiate in human or livestock populations. The population of insect carriers in temperate and tropical areas of the world creates a constantly renewing reservoir of infection. Furthermore, the armament of drugs utilized to inhibit and suppress the proliferation of these parasites gradually loses its efficacy due to the evolution of resistant protozoal strains. A complete cure of the infected hosts is still more difficult due to the multi-stage character of the protozoal life cycle.

The chemotherapeutic agents utilized in treatment of human malaria appear to act in one of two ways. The first proposed mechanism responsible for the action of the oldest known antimalarial agent, quinine, is that of nonspecific DNA binding or intercalation. The second proposed mechanism is specific to protozoal diseases and presumably inhibits protozoal growth by enzyme antagonism.

Protozoa apparently cannot utilize preformed folate or folic acid in their metabolic cycles and require a supply of para-aminobenzoic acid in order to synthesize their own supply of folic acid. As a consequence, folic acid enzyme antagonists have been found to show antiprotozoal activity. Interference with the enzymatic machinery in this synthetic pathway may be responsible for the selective antiprotozoal action of this class of drugs. Drugs which act in this fashion include chloroguanide, cycloguanil pamoate, pyrimethamine and its derivatives, as well as sulfamides and sulfones.

Among the folic acid antagonists, the biguanide members may be, in some cases, transformed in the host body to form active triazine metabolites. However, the triazine metabolite of chloroguanide has little or no usefulness in the therapy of humans and monkeys due to its rapid excretion from the body. Moreover, this latter class of compounds, that is, folic acid inhibitors, are most susceptible to a loss of efficacy due to the appearance of therapeutically resistant strains of protozoa. In fact, P. berghei is known as a pyrimethamine-resistant protozoal strain. Structural changes in the triazine rings of the presumably active form of these antiprotozoal drugs, as well as its method of administration, may modify the activity unpredictably as well as alter the rate of excretion of the drug from the host body. For example, while in malaria cases chloroguanide is rapidly excreted from the body when in its triazine form and has little or no usefulness, chloroguanide triazine pamoate, when tested with P.-berghei-infected mice, has good and lasting effects with a single muscular injection and is nt excreted rapidly from the host body. Owing to such unpredictability and the limited drugs available for treatment of human and animal diseases caused by blood-residing parasites, there is need for effective drugs for use in the treatment of these diseases.

1-(N-alkylamidino)-3-phenylureas were investigated by Curd et al. in the late 1940's for antimalarial activity against the malarial parasite Plasmodium gallinaceum in chicks. 1-(N-alkylamidino)-3-(p-chlorophenyl)ureas showed only anti-erythrocytic activity at high doses while 1(N-phenylamidino)-3-alkylureas showed no antimalarial activity whatsoever (Curd, F. H. S. et al., J. Chem. Soc. 1949, 1732). 1-amidino-3-phenylureas were investigated by Urbanski in 1960. This study indicated that of a large class of 1-amidino-3-(monosubstituted phenyl)ureas, the highest activity against the malarial parasite Plasmodium gallinaceum in chicks was obtained with 1-amidino-3-(4-nitrophenyl)urea (Skowronska-Serafin, B. and Urbanski, T., Tetrahedron, 10, 12–25 (1960)).

U.S. Pat. No. 3,539,616 to Wall discloses that 1-amidino-3-(di- and trisubstituted phenyl)ureas exhibit anti-malarial activity. The preferred phenyl substituents consisted of halogen or cyano. 2,6-substitution of the phenyl group attached to the 3-position of the urea was not disclosed.

In fact, a more recent publication of Goodfood, Walls et al., Br. J. Pharmac. 48, 650–654 (1973), indicated that subtituents ortho (i.e., 2′ or 6′ substitution) to the urea side chain of the phenyl group would exhibit low antimalarial activity.

The antiprotozoal uses of 1-(N-phenylamidino)-3-alkylureas and 1-amidino-3-phenylureas wherein the phenyl group is substituted at positions ortho to the urea side chain have been reported in U.S. Pat. No. 4,340,609.

1-phenyl-3-(N'-alkylamidino)thiourea compounds are known in the art. See Curd et al., J. Chem. Soc., p. 1732, 1739 (1949). A study in the 1940's by Curd of amidinothioureas resulted in a determination that they exhibit no antimalarial activity. However, it has now been found that novel classes of amidinothioureas possess valuable pharmaceutical properties.

SUMMARY OF THE INVENTION

This invention pertains to a novel class of amidinothiourea compounds, processes for their synthesis, and the treatment of humans and animals afflicted with gastrointestinal, spasmolytic, ulcerogenic and diarrheal disorders.

This invention also pertain to the treatment of humans and animals afflicted with parasitic infestations of the blood and blood-forming organs with compositions containing an effective amount of an antiparasitic amidinothiourea.

It is an object of this invention to provide a simple and effective method for the treatment of hypertension.

It is another object of this invention to provide an effective method for the treatment of gastrointestinal spasmolytic disorders in humans and mammals.

It is another object of this invention to provide an effective method for the treatment of gastrointestinal, secretory and ulcerogenic disorders in humans and mammals.

It is another object of this invention to provide a method for producing local anesthetic action in humans and mammals.

It is another object of this invention to provide a method for the treatment of diarrheal disorders in humans and animals.

It is another object of this invention to provide a method for the treatment of arrhythmia in humans and mammals.

It is a further object of this invention to provide an effective method for the treatment of parasitic infestations of humans.

It is a further object of this invention to provide an effective treatment for parasitic infestations of human blood and blood-forming organs.

It is a further object of this invention to provide an effective treatment for protozoal infestations of humans and, in particular, protozoal infestations responsible for malaria and malaria-type conditions.

It is a further object of this invention to provide effective antimalarial compositions and methods of treating humans exposed to malaria.

It is still a further object of this invention to provide an effective composition of amidinothiourea compounds active against folic-acid-antagonist-resistant strains of protozoa.

It is still a further object of this invention to provide an effective composition of an antiparasitic amidinothiourea useful in the treatment of veterinary parasitic diseases.

It is still a further object of this invention to provide an effective composition of amidinothiourea useful in the treatment of bovine piroplasmosis, bovine anaplasmosis, equine piroplasmosis, canine dirofilariasis, and related blood-residing diseases.

It is still a further object of this invention to provide compositions of amidinothioureas in combination with antibiotics, sulfur compounds and other agents effective in the treatment of protozoal infestations.

It is still a further object of this invention to provide an effective composition of an antiparasitic agent that has a long-lasting effect and is not quickly excreted from the host body.

DETAILED DESCRIPTION OF THE INVENTION

This invention describes a novel class of chemical compounds of the formula

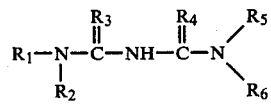

where, when $R_3=S$, then $R_4=NH$; and when $R_3=NH$, then $R_4=S$; where $R_1$ is substituted phenyl of the formula

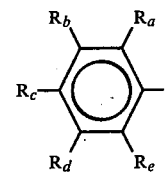

where $R_b$, $R_c$, $R_d$ and $R_e$ may be the same or different and are hydrogen, halo, loweralkyl, haoloweralkyl, nitro, loweralkoxy, hydroxy, aryloweralkoxy, acyloxy, cyano, haloloweralkoxy or loweralkylsulfonyl; provided that $R_a$ is halo, loweralkyl, haloloweralkyl, nitro, loweralkoxy, hydroxy, aryloweralkoxy, acyloxy, cyano, haloloweralkoxy or loweralkylsulfonyl; $R_2$ is hydrogen or loweralkyl; and $R_5$ and $R_6$ are hydrogen, loweralkyl, amino, loweralkylamino, loweralkyleneamino, haloloweralkyl, loweralkenyl, loweralkynyl, loweralkoxycycloalkyl, aralkyl, loweracylamino, acylalkylamino, loweracylalkylamino dipeptide; or $R_5$ and $R_6$ together form a 3–7 atom ring which may include 1–2 heteroatoms of N, O or S, and the nontoxic acid addition salts thereof.

In any discussion of the true structure of an amidinothiourea, tautomerism must be considered. It should be clear to anyone skilled in the art that the amidinothiourea side chain can be legitimately represented in any one of several tautomeric and geometric modifications.

The total number of possible variations in structure is quite high, but it is true to say that these variations can, and to some extent do, occur when these compounds are in solution.

One form may predominate over another depending upon the degree and location of substitution and on the nature of the solvent. The rates of conversion of one tautomer to another will depend upon the nature of the solvent, the degree of hydrogen bonding permitted, the temperature, and possibly other factors (such as pH, trace impurities and the like).

To illustrate what is meant by this, a number of likely structures are here shown for just one of the compounds of this invention:

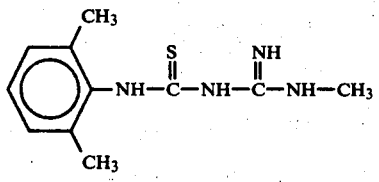

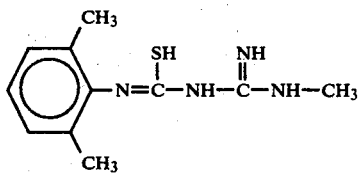

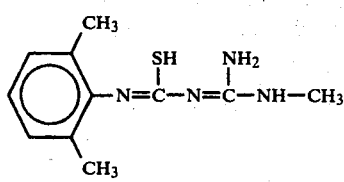

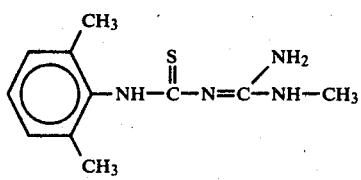

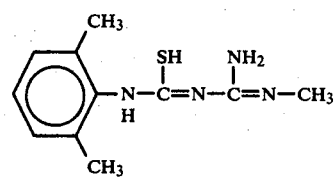

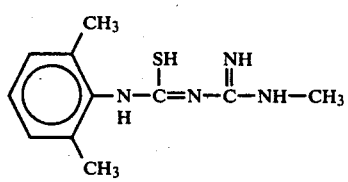

Of course, other types of structures are possible such as those with hydrogen bonding.

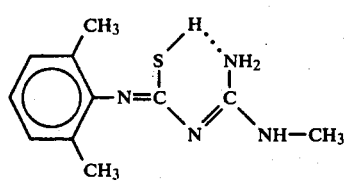

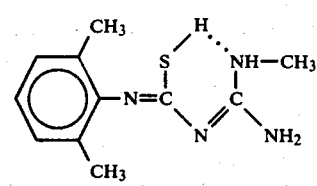

No attempt is made to exhaust the possible structures, for these are legion. The structures given are representative of the kind of phenomenon we are trying to describe and are encompassed within the scope of this invention.

It is predictable that in physiological conditions, any or all of these structures may exist or even predominate at the sites at which these molecules operate.

Compounds of this invention which are preferred include those where $R_1$ is substituted phenyl of the formula

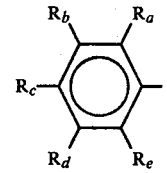

where $R_a$ and $R_e$ may be the same or different and are loweralkyl or halo; $R_b$ and $R_d$ may be the same or different and are hydrogen, alkoxy or halo; $R_c$ is hydrogen, halo, loweralkyl, cyano, nitro or alkoxy; and $R_5$ and $R_6$ are hydrogen, loweralkyl (either branched or unbranched), or diloweralkyl methyleneamine.

The most preferred compounds of this invention are those where $R_a$ and $R_e$ are methyl, ethyl, chloro or bromo; $R_b$ $R_c$ and $R_d$ are hydrogen, methyl, ethyl, hydroxy, methoxy, ethoxy, chloro or bromo; $R_5$ and $R_6$ are hydrogen, methyl, ethyl, propyl, i-propyl, butyl, i-butyl, sec-butyl, t-butyl, pentyl, hexyl, heptyl, or diloweralkyl methyleneamino.

A special embodiment of this invention comprises compounds which have $R_a$-loweralkyl substitution; $R_a$, $R_e$-di-loweralkyl substitution; $R_a$, $R_e$-loweralkyl, alkoxy substitution; $R_a$, $R_e$-loweralkyl, alkoxy substitution; $R_a$, $R_c$-loweralkyl, nitro substitution; $R_a$, $R_c$-diloweralkyl substitution; $R_a$, $R_c$, $R_e$-triloweralkyl substitution; $R_a$, $R_c$, $R_e$-loweralkyl, dihalo substitution; $R_a$, $R_c$, $R_e$-diloweralkyl, halo substitution; $R_a$, $R_e$-dihalo substitution; $R_a$, $R_c$-dihalo substitution; or $R_a$, $R_c$-loweralkyl, halo substitution.

Further special embodiments of this invention comprise a class of compounds in which $R_2$, $R_5$ and $R_6$ are hydrogen or loweralkyl substitution, and a class of compounds in which $R_2$ and $R_5$ are hydrogen or loweralkyl and $R_6$ is an alkyl group from 1 to 7 carbon atoms or an iminoalkyl group of the formula

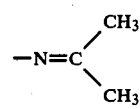

This invention further describes a novel method for the treatment of human and veterinary spasmolytic disorders, hypertensive conditions, gastrointestinal disorders and protozoal infestations by the administration of a compound of the formula

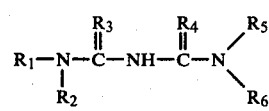

wherein $R_3$ is S and $R_4$ is NH, or wherein $R_4$ is S and $R_3$ is NH; and where $R_1$ is substituted phenyl of the formula

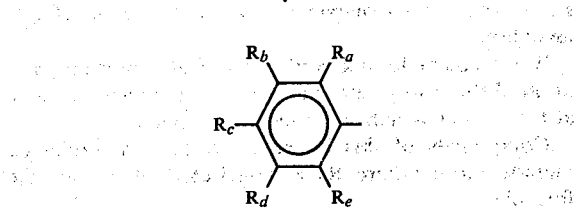

where $R_a$, $R_b$, $R_c$, $R_d$ and $R_e$ may be the same or different and are halo, loweralkyl, haloloweralkyl, nitro, loweralkoxy, hydroxy, aryloweralkoxy, loweralkylacyloxy, cyano, haloloweralkoxy or loweralkylsulfonyl; $R_b$, $R_c$, $R_d$ and $R_e$ may also be hydrogen; $R_2$ is hydrogen or loweralkyl; $R_5$ and $R_6$ are hydrogen, loweralkyl, cycloakyl, aralkyl, diloweralkylmethyleneamino, acylloweralkylamino or dipeptide; $R_5$ and $R_6$ together form a heterocycle selected from the group consisting of oxazolidinyl, thiazolidinyl, pyrazolidinyl, imidazolidinyl, piperidyl, piperazinyl, thiamorpholinyl, trimethylenetriaminyl, ethyleneiminyl and morpholinyl; where the heterocycle may be mono-, di-, tri- or tetra-substituted by hydrogen, lower alkyl, lower alkenyl, lower alkynyl, aryl, aralkyl, halo, nitro, cyano, sulfonyl, hydroxyl, carboxyl, lower alkanoyl, lower alkoxy, aryl lower alkoxy, halo lower alkoxy, amido, amino, lower alkylamino, aralkylamino, lower alkoxyamino, and aralkylamino; and the nontoxic acid addition salts thereof.

As employed above and throughout the disclosure, the following terms, unless otherwise indicated, shall be understood to have the following meanings:

"Alkyl" means a saturated aliphatic hydrocarbon which may be either straight- or branched-chain, preferably having no more than about 12 carbon atoms; and may be methyl, ethyl and structural isomers of propyl, butyl, pentyl, hexyl, heptyl, octyl, nonyl, decyl, undecyl and dodecyl; also included are the cycloalkyl groups such as cyclopropyl, cyclopentyl, cyclohexyl, etc., and the cycloalkylalkyl groups such as cyclopropylmethyl and the like.

"Loweralkyl" means an alkyl group as above, having 1 to 6 carbon atoms. Suitable loweralkyl groups are methyl, ethyl, n-propyl, isopropyl, butyl, sec-butyl, tert-butyl, n-pentyl, isopentyl and neopentyl.

"Cycloalkyl" means an aliphatic monocyclic saturated carbocyclic group having 3 to 6 carbon atoms, preferably cyclopropyl, cyclopentyl and cyclohexyl.

"Alkenyl" means an unsaturated aliphatic hydrocarbon having no more than about 12 carbon atoms and 1 to 3 carbon-carbon double bonds and which may include straight or branched chains, and may be any structural and geometric isomers of ethenyl, propylenyl, butenyl, pentenyl, hexenyl, heptenyl, octenyl, nonenyl, decenyl, undecenyl, and dodecenyl or butadienyl, pentadienyl, etc.; also included are the cycloalkylene groups such as cyclopropenyl, cyclopentenyl, cyclohexenyl, etc. and the cycloalkylalkylene groups such as cyclopropylenylmethyl, cyclohexenylmethyl and the like.

"Loweralkenyl" means alkenyl of 2 to 6 carbon atoms such as ethylene, propylene, butylene, isobutylene, etc., including all structural and geometrical isomers thereof.

"Alkynyl" means an unsaturated aliphatic hydrocarbon having no more than about 12 carbon atoms and containing one or more triple bonds, including any structural or geometric isomers of acetylenyl, propynyl, butynyl, pentynyl, hexynyl, heptynyl, octynyl, nonynyl, decynyl, undecynyl, dodecynyl, etc.

"Loweralkynyl" means alkynyl of 2 to 6 carbon atoms such as structural and geometric isomers of propargyl, butynyl, pentynyl, etc.

"Aryl" means phenyl and substituted phenyl.

"Substituted phenyl" means a phenyl group in which one or more of the hydrogens has been replaced by the same or different substituents including halo, loweralkyl, haloloweralkyl, nitro, amino, acylamino, hydroxy, loweralkoxy, arylloweralkoxy, acyloxy, cyano, haloloweralkoxy or loweralkylsulfonyl; the preferred substituted phenyl group is phenyl in which the 2- and 6-positions are substituted.

"Aralkyl" means an alkyl (preferably a loweralkyl) in which one or more hydrogens is substituted by an aryl moiety (preferably phenyl or substituted phenyl), e.g., benzyl, phenethyl, etc.

"Heterocycle" means a 3 to 7 membered ring having 1 to 3 heteroatoms which may be nitrogen, oxygen or sulfur, including pyridyl, pyrimidyl, pyrazolyl, imidazolyl, oxazolidinyl, thiazolidinyl, pyrazolidinyl, imidazolidinyl; piperazinyl, thiamorpholinyl, trimethylenetriaminyl, ethyleneiminyl, furyl, thienyl, oxazonelyl, thiazolyl, piperidyl, morpholinyl, etc.

"Substituted heterocycle" means a heterocycle in which one or more of the hydrogens on the ring carbons have been replaced by substituents as given above with respect to substituted phenyl.

"Dipeptide" means carboxylic residue of the condensation product of two amino acids selected from the group consisting of glycine, alanine, valine, leucine, isoleucine, phenylalanine, tyrosine, tryptophan, serine, threonine, methionine, cysteine, cystine, proline, hydroxy proline, aspartic acid, glutaric acid, lysine, arginine, and histidine.

The terms "halo" and "halogen" include all four halogens; namely, fluorine, chlorine, bromine and iodine. The halo alkyls, halophenyl and halosubstituted pyridyl include groups having more than one halo substituent which may be the same or different such as trifluoromethyl, 1-chloro-2-bromo-ethyl, chlorophenyl, 4-chloropyridyl, etc.

"Acyloxy" means an organic acid radical of lower alkanoic acid such as acetoxy, propionoxy, and the like.

"Loweralkanoyl" means the acyl radical of a loweralkanoic acid such as acetyl, propionyl, butyryl, valeryl, stearoyl, and the like.

"Alkoxy" is intended to include hydroxy alkyl groups, preferably loweralkyl groups such as methoxy, ethoxy, n-propoxy, i-propoxy, and the like.

The preferred "aralkyl" groups are benzyl and phenethyl.

The preferred "haloloweralkyl" group is trifluoromethyl.

The preferred "haloloweralkoxy" group is trifluoromethoxy.

It is well known in the pharmacological arts that nontoxic acid addition salts of pharmacologically active amine compounds do not generally differ in activities from their free base. The salts merely provide a convenient solubility factor.

The amines of this invention may be readily converted to their nontoxic acid addition salts by customary methods in the art. The nontoxic salts of this invention are those salts the acid component of which is pharmacologically acceptable in the intended dosages; such salts would incude those prepared from inorganic acids, organic acids, higher fatty acids, high molecular weight acids, etc., and include such as hydrochloric acid, hydrobromic acid, sulfuric acid, nitric acid, phosphoric acid, methane sulfonic acid, benzene sulfonic acid, acetic acid, propionic acid, malic acid, succinic acid, glycolic acid, lactic acid, salicylic acid, benzoic acid, nocotinic acid, phthalic acid, stearic acid, oleic acid, abietic acid, etc.

The nomenclature hereafter applied to the compounds of this invention is as follows:

Type I

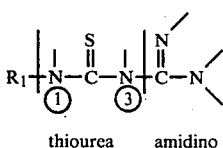

thiourea    amidino

Type II

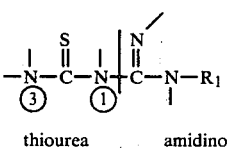

thiourea    amidino

The compounds of this invention may be prepared by the following general synthesis: for (Type I) compounds wherein $R_2=H$, $R_3=S$ and $R_4=NH$, condensation of a substituted phenyl isothiocyanate (prepared from an appropriate aniline and thiophosgene or diimidazolethiocarbonyl) with an appropriately substituted guanidine results in a 1-substituted phenyl-3-amidinothiourea according to Scheme I. The reaction is carried out in a polar medium using solvents such as dimethylformamide, tetrahydrofuran, etc. It is convenient to carry out the reaction by preparing the isothiocyanate in the reaction media and then forming guanidine in situ by hydrolyzing guanidine carbonate with base.

Substituted phenyl isothiocyanates are preferred reagents.

Scheme I

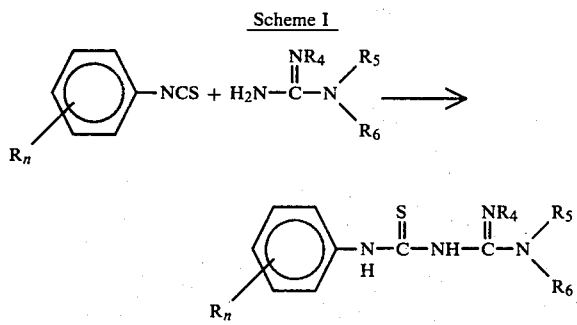

When it is desired to have $R_2$ substitution at the N-1, the starting material will be a secondary amine or preferably an aniline having N-alkyl substitution. Reaction with sodium thiocyanate results in a thiourea which is then reacted with an appropriately substituted cyanamide compound to prepare the amidinothiourea (Scheme 2).

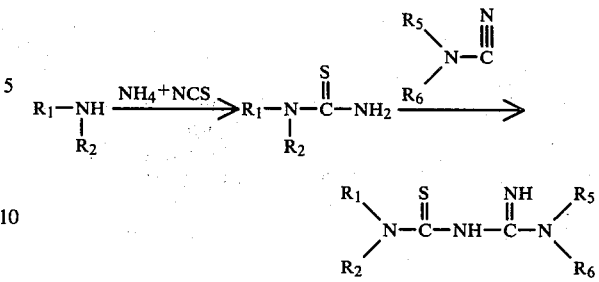

The starting anilines are either known, may be prepared by known techniques, or reference to the preparation is shown. Thus, chlorination or bromination of an acetanilide or aniline may be carried out in acetic acid, or in the presence of a small amount of iodine dissolved in an inert solvent such as carbon tetrachloride. A solution of chlorine or bromine is then added while the temperature is held near 0° C. Iodination may also be carried out by known methods using iodine monochloride (Cl I).

Alkylation may be carried out on an acetanilide using an alkyl halide and aluminum chloride under Friedel-Crafts conditions to obtain desired alkyl substitution.

Nitration may be carried out using fuming nitric acid at about 0° C.

A nitro compound may be hydrogenated to the corresponding amine which may then be diazotized and heated in an alcohol medium to form the alkoxy compound.

An amino compound may also be diazotized to the diazonimum fluoroborate which is then thermally decomposed to the fluoro compound.

Diazotization followed by a Samdmeyer-type reaction may yield the bromo, chloro or iodo compound.

When an amino compound is diazotized, followed by reaction with potassium ethylxanthate and then hydrolyzed, the mercapto compound results. This in turn may be alkylated to the alkylthio group which is then oxidized to the corresponding alkylsulfonyl substituent.

A chloro, bromo or iodo compound may also be reacted with trifluoromethyliodide and copper powder at about 105° C. in trifluoromethylformamide to obtain a trifluoromethyl compound [Tetrahedron Letters: 47, 4095 (1959)]. A halo compound may also be reacted with cuprous methanesulfinate in quinoline at about 150° C. to obtain a methylsulfonyl compound.

When it is desired that the final product contain an hydroxy group, it is preferred that the starting aniline contain the corresponding acyloxy or aralkyloxy groups. These may be prepared in the usual fashion by acylating the starting hydroxy aniline compound with an acyl halide or anhydride in the presence of a tertiary amine or aralkylating with an aralkyl halide or sulfate. Of course, the amine function would be protected in the customary manner. Hydrogenation to the desired hydroxy compound may then take place after the formation of the amidinourea. This may be accomplished with a metal catalyst (Pd/C, Pt, etc.) in a polar medium (ethanol, THF, etc.), sodium in liquid ammonia, etc. Thus, for example, the 3,4-dihydroxy amidinothiourea compound may be prepared from the corresponding 3,4-dibenzyloxyaniline. The hydroxy compounds may also be prepared by hydrolysis of the acyl or aralkoxy compounds with acid.

Reactions may also be carried out at other stages of synthesis depending on the substituents present and the substituents desired, and various combinations of the foregoing reactions will be determined by one skilled in the art in order that the desired product results. Thus, a phenylamidinothiourea may be halogenated or nitrated as above, etc.

The Type II compounds of this invention may be prepared by the following general synthesis:

Condensation of cyanamide and a substituted aniline results in the corresponding substituted phenylguanidine.

The reaction is preferably carried out on the aniline salt either in a polar medium or neat and using increased temperatures. The salt used may be any acid addition amine salt, but preferably the salt of a mineral acid. The polar medium may be aqueous, partially aqueous, or a nonaqueous solution. It is convenient to choose a solvent that will reflux at the desired reaction temperature. The more preferred solvents are water or alcohol, but other solvents may be used, such as DMSO, diethyleneglycol, ethyleneglycol, tetrahydrofuran, dimethylformamide, etc. The most preferred solvent is a mildly acidic solvent which is nonnucleophilic, such as phenol, cresol, xylenol, etc. The reaction should also be carried out at a temperature which is high enough so that condensation takes place readily, but not sufficient to decompose the guanidine formed. The reaction temperature can vary from room temperature to about 250° C., although it is preferable to run the reaction at temperatures from about 50° C. to 150° C. The guanidine salt which is formed can be converted to the free base with a metal hydroxide or alkoxide solution. The isolation of the desired guanidine can be carried out by any method known in the art.

When the substituted phenylguanidine is reacted with a substituted isothiocyanate of the formula R'NCS, then the product formed in a 1-substituted phenylamidino-3-R'thiourea. This reaction is preferably carried out in a nonpolar medium using solvents such as benzene, toluene, xylene, etc. The reaction is also carried out as above at raised temperatures.

The following reaction equations illustrates this synthesis:

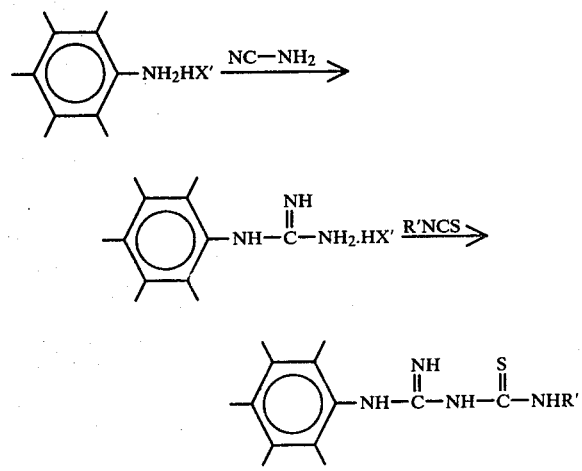

where HX' is a mineral acid and R' is other than hydrogen.

When R substitution is desired in the N-position, it is convenient to carry out the condensation using the appropriately N-substituted aniline. Thus, for example, N-methyl-2,6-dimethylaniline would result in the 1-(2,6-dimethylphenyl)-1-methylguanidine. This is then reacted as above with the isothiocyanate to form the amidinothiourea.

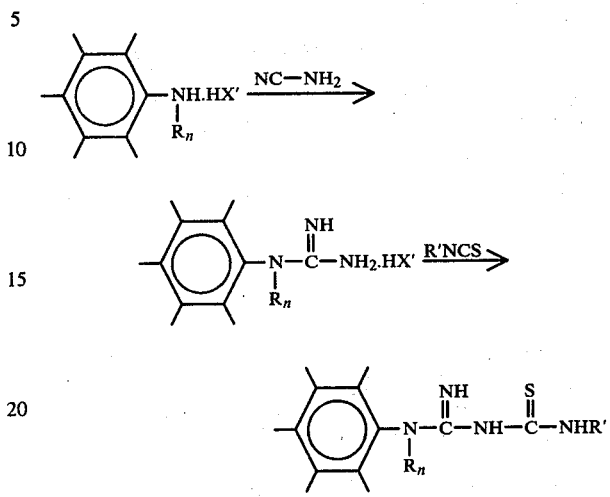

It is convenient to use t-butylisothiocyanate in the above reaction where R' is not desired in the 1-position. This may then be selectively hydrolyzed off.

The isothiocyanates used in this reaction may be alkyl, cycloalkyl, phenyl or substituted phenylisothiocyanates. Examples are listed in Table I. This table should not be construed to limit the isothiocyanates or the amidinothioureas embraced within the present invention.

Table I ethylisothiocyanate
propylisothiocyanate
i-propylisothiocyanate
butylisothiocyanate
pentylisothiocyanate
hexylisothiocyanate
octylisothiocyanate
propargylisothiocyanate
methallylisothiocyanate
cyclopropylisothiocyanate
cyclobutylisothiocyanate
cyclopentylisothiocyanate
cyclohexylisothiocyanate
cyclohex-2-enylisothiocyanate
acetylisothiocyanate
propionylisothiocyanate
benzoylisothiocyanate
phenylisothiocyanate
benzylisothiocyanate
phenethylisothiocyanate
cyclopropylmethylisothiocyanate
cyclopropylethylisothiocyanate The compounds of this invention have a useful degree of gastric antisecretory activity and are effective in reducing the volume and the acidity of the gastric fluid in humans and mammals. Further, these compounds produce a considerable spasmolytic action on the gastrointestinal musculature, i.e., they reduce the peristaltic action of the gastrointestinal musculature which is manifested by a delay in gastric emptying time. It should further be noted that these compounds are also characterized by their low acute oral toxicity.

In particular, the amidinothioureas as herein described are useful in the treatment of such gastrointestinal disorders and diseases as duodenal ulcer and peptic ulcer. The compounds of this invention are also useful as antidiarrheal agents.

The instant compounds may be used alone or in combination wtih other known antacids such as aluminum hydroxide, magnesium hydroxide, magnesium trisilicate, aluminum glycinate, calcium carbonate and the like.

The compounds of this invention possess blood-pressure-lowering activities and are useful an antihypertensive agents.

The compounds described herein also possess useful antiarrhythmic properties as well as useful local anesthestic properties.

For all these purposes, the amidinothioureas of this invention can be normally administered orally, parenterally or rectally. Orally they may be administered as tablets, aqueous or oily suspension, dispersible powders or granules, emulsions, hard or soft capsules, or syrups or elixirs. Parenterally they may be administered as a salt in solution which pH is adjusted to physiologically accepted values. Aqueous solutions are preferred.

Compositions intended for oral use may be prepared according to any method known to the art for the manufacture of pharmaceutical compositions, and such compositions may contain one or more agents selected from the group consisting of sweetening agents, flavoring agents, coloring agents, preserving agents and the like, in order to provide a pharmaceutically elegant and palatable preparation.

The dosage regimen in carrying out the methods of this invention is that which ensures maximum therapeutic response until improvement is obtained, and thereafter the minimum effective level which gives relief. Thus, in general, the dosages are those that are therapeutically effective in the treatment of gastrointestinal disease conditions or symptoms, such as duodenal ulcer, peptic ulcer or diarrhea, and in the alleviation of hypertensive and arrhythmic disorders. The therapeutically effective doses correspond to those dosage amounts found effective in tests using animal models which are known to correlate to human activity for each particular disorder. In general, it is expected that daily doses between about 0.25 mg/kg and 50 mg/kg (preferably in the range of 0.5-10 mg/kg/day), will be sufficient to produce the desired therapeutic effect, bearing in mind, of course, that selecting the appropriate dosage in any specific case, consideration must be given to the patient's weight, general health, age, the severity of the disorder, and other factors which may influence response to the drug.

Various tests in animals have been carried out to show the ability of the compounds of this invention to exhibit reactions that can be correlated with activity in humans. These tests involve such factors as the effect of the amidinothioureas on gastric secretion, their spasmolytic effect, their blood-pressure-lowering effect and determination of their toxicity. It has been found that the compounds of this invention when tested in the above variety of situations show a marked activity.

One such test is the gastric secretion test. This test is carried out as follows: Shay rats are fasted for 4-8 hours and water is given ad lib. The rats are selected at random and separated into groups of ten. The animals are treated intraduodenally (I.D.) with the test compound or the vehicle immediately subsequent to the ligation of the stomach at the pyloric sphincter. The animals are sacrificed with chloroform at 4 hours post-drug-administration, the stomach removed and its contents are assayed for volume, pH and total acids.

A second gastric secretion test is carried out on the dog. This is outlined in the *Handbook of Physiology*, Section 6: Alimentary Canal, Volume II: Secretion. American Physiology Society, Washington, D.C., 1967.

It has been found that the compounds of this invention, when subjected to the above gastric secretion tests, display marked ability to decrease gastric volume and gastric acidity. These tests are known to correlate well with gastric activity in humans and are standard tests used to determine antisecretory properties.

To determine the antiulcer effectiveness, the following test is employed: Male Wistar rats (130–150 grams) are fasted for 24 hours, then given reserpine at 5 mg/kg i.p. Twenty-four hours later, the stomachs are removed and examined for ulceration. Ulcers are graded on a 0–4 scale and the number of ulcers is recorded. Pretreatment with the amidinothiourea compounds produces a decrease in ulcer grade and the number of ulcers compared to the control reserpine-treated rats.

Determination of antispasmolytic properties can be carried out by the procedure a outlined by D. A. Brodie and S. K. Kundrats in their article entitled "Effect of Drugs on Gastric Emptying in Rats," *Fed. Proc.* 24:714 (1965) Acute toxicity is calculated according to the standard Litchfield-Wilcoxon procedure.

In view of the results of these tests, the pharmacological data clearly indicates that the amidinothioureas of this invention can be considered to be active gastric antisecretory and antispasmolytic agents which are substantially free of anticholinergic side effects and having a low toxicity.

The compounds described in this application are useful antidiarrheal agents. For these purposes they can be administered orally, parenterally or rectally. Administration by the oral route is preferred. Orally these compounds may be administered in tablets, hard or soft capsules, aqueous or oily suspensions, dispersible powders or granules, emulsions, syrups or elixirs. The optimum dosage, of course, will depend on the particular compound being used and the type and severity of the condition being treated. In any specific case, the appropriate dosage selected will further depend on factors of the patient which may influence response to the drug; for example, general health, age, weight, etc., of the subject being treated.

Although the optimum quantities of the compounds of this invention to be used as antidiarrheal agents will depend on the compound employed and the particular type of disease condition treated, oral dosage levels of preferred compounds when administered to a mammal in dosages of 0.01 to 500 mg/kg of body weight per day are particularly useful. The preferred range of 0.05 to 200 mg/kg. Comparative dosages may be used in parenteral or rectal administration.

Compositions intended for oral use may be prepared according to methods known to the art for the manufacture of pharmaceutical compositions. Such compositions may contain one or more agents selected from the group consisting of sweetening agents, flavoring agents, coloring agents, preserving agents, etc., in order to provide a pharmaceutically elegant and palatable preparation.

Further, the active amidinothiourea may be administered alone or in admixture with other agents having the same or different pharmacological properties.

The composition may contain such selected excipients as inert diluents such as calcium carbonate, lactose, etc.; granulating and disintegrating agents such as maize starch, alginic acid, etc.; lubricating agents such as magnesium stearate, etc.; binding agents such as starch gelatin, etc.; suspending agents such as methylcellulose, vegetable oil, etc.; dispersing agents such as lecithin, etc.; thickening agents such as beeswax, hard paraffin, etc.; emulsifying agents such as naturally occurring gums, etc.; nonirritating excipients such as cocoa butter, polyethylene glycols, etc.; and the like. Further, in formulating these compounds, for every 100 parts by weight of the composition, there may be present between 5 and 95 parts by weight of the active ingredient. The dosage unit form will generally contain between 0.1 mg and about 500 mg of the active ingredients of this invention. The preferred unit dose is between 1 mg and about 50 mg. The compositions may be taken 1-8 times daily, depending on the dosage unit required.

Various tests can be carried out in animal models to show the ability of the amidinothioureas of this invention to exhibit reactions that can be correlated with antidiarrheal activity in humans. The following tests show the ability of the compounds of this invention to inhibit diarrhea in animals and are known to correlate well with antidiarrheal activity in humans. These are considered to be standard tests used to determine antidiarrheal properties. This correlation can be shown by the activities of compounds known to be clinically active. In view of the results of these tests, the amidinothioureas of this invention can be considered to be antidiarrheal agents.

1. Fecal output in rat: The oral $ED_{50}$ (that dose which would be expected to reduce fecal output by 50%) is determined by a method described by Bass et al., 1972. Briefly, the method involves dosing the rats and collecting the fecal output over an 8-hour period (4 P.M.-12 midnight) with the room darkened starting at 4:30 P.M.

Ref: Bass, P., Kennedy, J. A. and Willy, J. N.: Measurement of fecal output in rats. Am. J. Dig. Dis. 10:925–928, 1972.

2. Castor oil test in mice: Groups of mice are orally dosed with test compound and a half hour later all mice are given 0.3 ml of castor oil. Three hours after castor oil administration, all mice are checked for diarrhea and the dose of testing compound which protected 50% of the mice for diarrhea is the $ED_{50}$ dose.

3. Castor oil test in rats: The test is conducted according to Niermegeers et al., 1972. The rat is orally dosed with graded doses of test compound. One hour after dosing, each animal is challenged with 1 ml of castor oil orally. Fecal output is examined 1, 2, 3, 4, 6 and 8 hours after castor oil. Absence of diarrhea is the criterion of drug effectiveness.

Ref: Niemegeers, C. J. E., Lenaerts, F. M. and Janssen, P. A. J. Difenoxine, a potent, orally active and safe antidiarrheal agent in rats. *Arzneim-Forschung* (Drug Res.) 22, 516–1518, 1972.

Tests in animals have also been carried out to show the ability of compounds of this invention to inhibit reactions that can be correlated with antihypertensive effects in humans. One such test is outlined by Jacques de Champlain, Lawrence R. Krahoff and Julius Axelrod in *Circulation Research* XXIII:479 (1968). This testing method is known to correlate well with antihypertensive activity in humans and is a standard test used to determine antihypertensive properties. In view of the results of this test, the amidinothioureas of this invention can be considered to be active antihypertensive agents.

Various tests can be carried out in animal models to show the ability of the amidinothioureas of this invention to exhibit reactions that can be correlated to antiarrhythmic properties and local anesthetic activity in humans. The following tests show the ability of the compounds of this invention to produce local anesthetic actions in animals and are known to be clinically active. In view of the results of these tests, the amidinothioureas of this invention can be considered to be local anesthetic agents.

Harris Dog Induced Arrhythmia

In 1950, Harris published a technique for induction of acute myocardial infarction in dogs which has become accepted as a useful method for studying the efficacy of anti-arrhythmic agents. Generally, ventricular arrhythmias arise four to eight hours after acute myocardial infarction and persist for 48 to 72 hours. It is felt that the arrhythmias orginate in subendocardial Purkinje cells within or near the site of the infarction and are due to enhanced automaticity within these cells. This model has been employed for the evaluation of oral anti-arrhythmic efficacy of the amidinothioureas of this invention.

Methods

Healthy male mongrel dogs 9.5-15 kg. were anesthetized with intravenous sodium pentobarbital (30 mg/kg) and the trachea was intubated and respired with room air with a Harvard respirator. Under aseptic conditions, the chest was opened through a small left thoractomy at the fourth or fifth intercostal space and the pericardium incised near the left atrial appendage. The left anterior descending coronary artery was isolated approximately 5-10 mm distal to the left atrial appendage without traumatizing the associated coronary vein. A double ligature was passed under the coronary artery. One of the ligatures was firmly tied around a 20 g needle barrel overlying the coronary artery, and the needle immediately extracted. This procedure results in a 20-50% constriction of the coronary artery at the site of the ligature. After twenty minutes, the second ligature was tied in order to complete occlude the distal portion of the left anterior coronary artery. The lungs were then expanded. The chest wall was closed and the thoracic evacuated. The dogs were allowed to recover from anesthesia with supplementary morphine or Tranvet (propiopromazene HCl) administered as needed to prevent unneccessary pain. Antibiotics were given prophylactically.

Eighteen to 24 hours after surgery, the dogs were placed in cages in a quiet environment with water constantly available. At this time the dogs were able to walk freely around the cage and showed no signs of obvious discomfort. The Lead II electrocardiogram was monitored continuously and recorded on a Beckman Dynograph recording system. Recordings were made on a scheduled basis before and after administration of gelatin capsules containing the amidinothiourea (10 mg/kg) or placebo. Normal and abnormal beats were counted and expressed as a ratio of normal beats/total beats per unit time. Only beats of sinoatrial origin were considered normal.

The dogs were generally given the first capsule after recording the EKG for 40-60 minutes. After three hours a second capsule was given and EKG's were monitored for an additional three hours. The dogs were then fed. Forty-eight hours after surgery, the dogs were again monitored according to the schedule employed on the first day.

At the end of the second day, the dogs were sacrificed with an intravenous overdose of sodium pentobarbital. Hearts were extracted and examined to determine the size and area of the induced infarct.

Additional tests are discussed in U.S. Pat. No. 4,178,387, the disclosure of which is incorporated herein by reference.

The tests employed to determine the separation of local anesthetic and cardiovascular activity at effective antidiarrheal doses with representative compounds of this invention are as follows:

Several different procedures generally employed in testing for local anesthetic activity are used to determine local anesthetic effects. These tests have been extensively used in the past and have given satisfactory results in defining the local anesthetic properties of compounds.

A discussion of experimental methods for evaluating local anesthetic properties of drugs is found in *Evaluation of Drug Activities: Pharmacometrics*, Vol. 1, Ed. by D. R. Lawrence and A. L. Bacharach, Academic Press, Inc. (London) Ltd. (1964). Applicants hereby incorporate by reference Chapter 9 of this book entitled "Local Anesthetics," pp. 204-214.

Tests which show the lack of side effects of the preferred antidiarrheal compounds include the following:

1. Effect on Hexobarbital-Induced Loss of Righting Reflex

The test compound and a vehicle given orally thirty minutes before hexobarbital were compared for their effect on the duration of the loss of righting reflex (failure to right within five seconds) induced in groups of Swiss Webster mice (10/group, 18-20 g) by the intraperitoneal injection of hexobarbital (100 mg/kg, 1.P.).

2. Effect on Plasma Glucose in Rats

Groups of 5-10 male Sprague-Dawley rats (170-210 g) were orally dosed with the test compound or the vehicle. Three hours after dosing, the rats were sacrificed by decapitation and blood was collected for plasma glucose evaluation.

3. Effect on Inducing Emesis in Dogs

Female beagle dogs (6-10 kg) were randomly selected for intravenous dosing with the test compound. Each dose of the test compounds was given to either two or four dogs. Immediately after the injection, the dogs were observed for emesis for a period of up to one hour.

An additional test method used to examine the unique local anesthetic activity of the novel compounds of this invention involves direct application to the isolated desheathed sciatic-perineal-tibial trunk of the bullfrog. The methodology used is as follows:

All drug solutions were applied to 15 mm segments of desheathed trunks situated between stimulating and recording electrodes employing a standard pharmacologic technique for observing the condition blocking effects of local anesthetics.

Briefly summarized, the technique allows nerve impulses to be initiated by means of an electrical stimulus applied to a drug-free segment of a trunk and to be conducted through the treated segment. Recording electrodes placed on the distal side of the treated segment detect only those impulses that were conducted through the 15 mm segment. By relating the amplitude of the recorded compound spike potential to that recorded before the application of drug treatment, an index is available for the proportion of fibers that could conduct impulses through 15 mm of treated length. This index is referred to as "percent of control spike height" or "percent reduction of spike height" or "percent block of conduction."

The source of the nerves is the bullfrog, *Rana castesbeiana*. During dissection, the nerves are exposed to Ringer solution having the following composition: 110 mM NaCl, 3.0 mM KCl, 1.8 mM $CaCl_2$, 20 mM $NaHCO_3$, 2 mM phosphate buffer. The solution is bubbled with 95% $O_2$, 5% $CO_2$ to maintain a pH of $7.2\pm0.05$ at room temperature (22°-24° C.).

Preparation of Ringer solution with test substance:

First, a quantity of drug is weighed out which would make a 50 mM solution when dissolved in 5.0 ml of Ringer. The drug is dissolved in 0.4 ml of absolute ethanol by stirring for ten minutes at high speed on a Genie Vortex apparatus. The solution is then brought to 5.0 ml with standard Ringer solution. The drug solution is then diluted ten times with Ringer solution to give a final concentration of 5.0 mM. The final solution is bubbled with 95% $O_2$, 5% $CO_2$ to give a pH of 7.2. The final concentration of ethanol is 0.172 M.

To control for the ethanol in the drug solution, the drug-free Ringer solution used to recover nerves from drug effect was made with the same final concentration of ethanol. This ethanol had no effect on conduction.

The same general procedure was used to prepare a solution of the test drug in a dimethylsulfoxide Ringer solution. The final concentration of diemthylsulfoxide (DMSO) was 0.101 M. DMSO had no effect on conduction.

Uterine Muscle Spasm Inhibition

The test protocol described below utilizes generally accepted methods to show the ability of the compounds of this invention to inhibit uterine muscle spasm in animal models and are known to correlate well with antispasmodic activity in humans.

(a) Female virgin Wistar rats at an average weight of 160-220 g are used for the experiment. Prior to the experiment, the animals are housed five per group and maintained according to standard animal husbandry procedures. The animals are treated with DES (100 mg/kg/body weight) 24 hours prior to the experiment. The stage of estrus cycle is determined by vaginal smears on the morning of the experiment.

(b) Rats in estrus are killed by a blow on the head and the abdomen is opened. The two horns of the uterus are dissected out and transferred to a dish containing Bathing's solution (composition in g: NaCl 8.046; KCl, 0.20; $CaCl_2.2H_2O$, 0.132; $MgCl_2.6H_2O$, 0.106; $NaCHO_3$, 1.0; $NaH_2PO_4$, 0.065; dextrose, 1.0 distilled to 1 liter with distilled water). The two horns are separated and freed from mesentery in Bathing's solution. A thread is attached at each end of each horn and the uterine segment is mounted in a tissue bath (50 ml) maintained at 37° C. by a circulatory bath and aerated with 95% $O_2$, 5% $CO_2$.

One thread is attached to a fixed pin and the other to a transducer.

(c) Contractions are recorded isometrically on a Beckman dynograph in conjunction with a Grass force-displacement transducer (FTO3C) which has been calibrated in g tension, or isotonically in conjunction with a Harvard smooth muscle transducer (386). The tissue is subjected to a baseline tension of 0.5 g. The preparation is allowed to equilibrate for thirty minutes prior to the experiment.

(d) Various spasmogens such as acetylcholine chloride, $PGF_{2\alpha}$, $PGE_2$, oxytocin, $BaCl_2$ or ergonivine maleate may be used to induce contractions in the isolated uterine strip in accordance with a general In Vitro Methodology for Evaluation of Compound Effect on Isolated Guinea Pig Ileum for description of obtaining dose-response curve.

(e) After the control dose-response curve is obtained, the tissue is allowed to relax for five minutes before the addition of the spasmolytic drug (inhibitory drug). The test drug is in contact with the tissue for two minutes before the dose-response curve is repeated. The inhibitory effect of the test drug is determined as follows:

$$\% \text{ maximum response} = \frac{\text{g tension developed with spasmogen + test drug}}{\text{g tension developed with spasmogen}} \times 100$$

The % maximum response is calculated for each dose of the dose-response curve and the control and drug curves are plotted.

The dose-response behavior on the isolated gravid rat uterus of acetylcholine chloride, oxytocin and $PGF_{2\alpha}$ is compared in the presence and absence of varying doses using the noncumulative dose response method. The stimulatory effect of these spasmogens on the isolated gravid rat uterus preparation is recorded using the isometric method to record the contractions induced.

The novel amidinothioureas of this invention are useful in the treatment of parasitic infestations of a human host, particularly parasitic protozoal infestations in the genus Plasmodium.

Novel amidinothioureas are also useful in the veterinary treatment of blood-residing diseases afflicting cattle, horses, sheep and dogs.

These compounds are useful in the treatment of veterinary diseases caused by parasitic helminths, particularly Filaria, and by parasitic protozoa, particularly Plasmodium and Babesia.

Microbiological tests can be carried out in model systems to show the ability of the amidinothioureas of this invention to exhibit activity that can be correlated with antiprotozoal activity in humans and animals. The following microbiological test can show the ability of the compounds of this invention to inhibit parasitic protozoal growth and reproduction.

Antimalarial Blood Smear Test

Mice are injected intraperitoneally with 5,000,000 parasitized blood cells from a donor. Groups of 10 mice receive inoculations administered subcutaneously in doses ranging from 0.15 to 100 mg/kg, suspended in 0.5% methecel solution (doses expressed as base). The compound of interest is repeatedly injected on the day of inoculation (Day 1), Day 2 and Day 3. Blood smears are performed on Days 4, 5, 6 and 10 and the number of parasitic protozoa noted.

The compounds of this invention are also useful chelating agents for treating patients suffering from metal poisoning, for example, poisoning by magnesium, arsenic, chromium, manganese, cobalt, nickel, copper, zinc, cadmium, silver, lead, antimony and mercury, by administering to a patient suffering from metal poisoning a therapeutically effective amount between 0.5 mg and 500 mg per dosage unit of at least one of said compounds.

The compounds of this invention are also useful as chelating agents for the processing of solutions or slurries of heavy metal salts and coordination complexes. The chelating agents disclosed herein are useful in processes for the purification of heavy metal complexes, the selective separation of heavy metal atoms from metal mixtures, and the treatment of industrial wastes.

The following are detailed examples which show the synthetic preparation of the compounds of this invention. They are to be construed as illustrations of said compounds and not as limitations thereof.

EXAMPLE 1

Preparation of 1-(2,6-dimethylphenyl)-3-methylamidinothiourea

To a stirred suspension of 7.3 g (30.0 mmol) of methylguanidine sulfate in THF (100 ml) was added 4.8 g (60.0 mmol) of 50% W/W aqueous NaOH, the mixture stirred for one hour after which 5.0 g of anhydrous $Na_2SO_4$ were added and the mixture stirred for an additional hour. To the mixture was added dropwise over one hour a solution of 2,6-dimethylphenylisothiocyanate (4.9 g, 30.0 mmol) in THF (40 ml). The mixture was allowed to stir at ambient temperature overnight. The THF was removed under vacuum and the residue partitioned between $H_2O$ and $CHCl_3$ and the aqueous layer extracted with $CHCl_3$ (1×100 ml). The extracts were dried ($MgSO_4$) and concentrated to give a yellow oil which was dissolved in MeOH and acidified with HCl/MeOH. The MeOH was evaporated to give a yellow gum which was crystallized from $CH_3C\equiv N$ to give 6.5 g of the desired hydrochloride salt.

EXAMPLE 2

Preparation of 1-(2,6-diethylphenyl)-3-methylamidinothiourea

To a stirred suspension of 7.3 g (30.0 mmol) of methylguanidine sulfate in THF (100 ml) was added 4.8 g (60.0 mmol) of 50% W/W aqueous NaOH. The mixture was stirred for one hour after which 5.0 g of anhydrous $Na_2SO_4$ was added and the mixture stirred for an additional hour. To the mixture was added dropwise over one hour a solution of 5.7 g (30.0 mmol) of 2,6-diethylphenylisothiocyanate in THF (40 ml) and the mixture was stirred for two hours at ambient temperature. The THF was removed under vacuum and the residue partitioned between $H_2O$ and $CHCl_3$. The layers were separated and the aqueous layer extracted with $CHCl_3$ (1×100 ml). The extracts were dried ($MgSO_4$) and concentrated to give a yellow oil which was dissolved in MeOH and acidified with HCl/MeOH. The MeOH was removed under vacuum to give a viscous yellow oil which slowly crystallized on standing. Crystallization from $MeOH/CH_3C\equiv N$ gave 8.5 g (94%) of the desired salt.

EXAMPLE 3

Preparation of 1-(2,6-diethylphenyl)-3-amidinothiourea 17.6 g of an aqueous 50% NaOH solution was added to guanidine carbonate (19.8 g) in THF. The mixture was stirred for four hours after which 10 g of 2,6-diethylphenylthiocyanate in 100 ml of THF was added dropwise. The mixture was stirred overnight.

The reaction mixture was concentrated, 100 ml of $H_2O$ and 10 ml of 50% aqueous NaOH added. After extraction with 600 ml of EtOAc, the extract was washed with NaCl saturated $H_2O$, dried ($Na_2SO_4$) and filtered. The filtrate was concentrated to 250 ml and 80 ml of $HCl/Et_2O$, 150 ml of $Et_2O$ added. Crystals formed on standing. The crystals were washed with $Et_2O$ and dried for one hour to give 10.8 g of amidinothiourea hydrochloride.

EXAMPLE 4

Preparation of 1-(2-chloro-6-methylphenyl)-3-methylamidinothiourea hydrochloride To a stirred suspension of 9.8 g (40 mmol) of methylguanidine sulfate in 200 ml of THF was added 6.5 g (82 mmol) of 50% aqueous NaOH. The mixture was stirred for one hour after which 5 g of anhydrous $Na_2SO_4$ were added and the mixture stirred an additional 0.5 hour. To the mixture was added dropwise a solution of 7.3 g (40 mmol) of 2-chloro-6-phenylisothiocyanate in 50 ml of THF over a period of one hour. The solution was stirred another 1.5 hours. The reaction mixture was filtered and the filtrate concentrated in vacuo. The residue was washed into a sep. funnel with $CHCl_3$ as a white solid and washed with $H_2O$ (2×200 ml). Aqueous layers were combined and back-washed with $CHCl_3$. All organic phases were combined and dried ($MgSO_4$).

The dried $CHCl_3$ solution was filtered and evaporated in vacuo to give a yellow oil. The oil was dissolved in MeOH and acidified with HCL/MeOH. The MeOH was removed in vacuo and the crystalline foam which remained was recrystallized from $CH_3CN$ (210 ml) and MeOH (15 ml) to yield a solid. The solid was vacuum dessicated at 100° for two hours and vacuum dessicated again at ambient temperature over the weekend to yield 7.39 g (63%) of the amidinothiourea hydrochloride.

EXAMPLE 5

Ten thousand tablets for oral use, each containing 50 mg of 1-(2',6'-dichlorophenyl)-3-methylamidinothiourea hydrochloride, are prepared from the following types and amounts of material:

| Ingredient | Grams |
|---|---|
| 1-(2',6'-dichlorophenyl)-3-methylamidinothiourea hydrochloride | 500 |
| Lactose U.S.P. | 350 |
| Potato starch U.S.P. | 346 |

The mixture is moistened with an alcoholic solution of 20 grams of stearic acid and granulated through a sieve. After drying, the following ingredients are added:

| Ingredient | Grams |
|---|---|
| Potato starch U.S.P. | 320 |
| Talcum | 400 |
| Magnesium stearate | 500 |
| Colloidal silicium dioxide | 64 |

The mixture is thoroughly mixed and compressed into tablets.

EXAMPLE 6

Five hundred ampoules each with 2 ml of solution which contain 15 mg of 1-(2-methyl-6-chlorophenyl)-3-methylamidinothiourea hydrochloride is prepared from the following types and amounts of materials:

| Ingredient | Grams |
|---|---|
| 1-(2-methyl-6-chlorophenyl)-3-methylamidinothiourea hydrochloride | 7.5 |
| Ascorbic acid | 1 |
| Sodium bisulphite | 0.5 |
| Sodium sulphite | 1 |

EXAMPLE 7

Capsules are prepared as follows:
- 15 g of 1-(2,6-diethylphenyl)-3-methylamidinothiourea hydrochloride,
- 3 g magnesium stearate,
- 2 g finely divided silica sold under the trademark CAB-O-SIL by Godfrey L. Cabot, Inc., Boston, Mass., and
- 369 g of lactose.

The ingredients are thoroughly mixed with each other and the mixture is filled in gelatin capsules. Each capsule contains 500 mg of the composition and thus 15 mg of 1-(2,6-diethylphenyl)-3-methylamidinothiourea hydrochloride.

EXAMPLE 8

50 g of 1-(2',6'-dimethylphenyl)-3-methylamidinothiourea hydrochloride, 5 g of propyl p-hydroxybenzoate are dissolved and diluted to 5,000 cc with twice distilled water after the addition of modified Sorensen buffer solution in an amount sufficient to adjust the pH value to a pH of 6.0. Sodium chloride is dissolved therein in an amount sufficient to render the resulting solution isotonic. The final solution is passed through a bacteriological filter and the filtrate is autoclaved at 120° C. for 15 minutes to yield a parenterally applicable solution which contains 50 mg of 1-(2',6'-dimethylphenyl)-3-methylamidinothiourea hydrochloride in 5 cc.

When 2,6-diethylphenylthiocyanate in Example 3 is replaced by the thiocyanates of the anilines of Table II below, then the corresponding products of Table III below are prepared.

Table II 2-methyl-6-chloroaniline
2-methyl-6-fluoroaniline
2-methyl-6-bromoaniline
2-methyl-6-iodoaniline
2-methyl-6-methoxyaniline
2-methyl-6-ethoxyaniline
2-methyl-6-ethylaniline
2-methyl-6-propylaniline
2-methyl-6-i-propylaniline 2-methyl-6-butylaniline
2-methyl-6-cyanoaniline
2-methyl-6-trifluoromethylaniline
2-methyl-6-nitroaniline
2-methyl-6-methylsulfonylaniline
2-ethyl-6-chloroaniline
2-ethyl-6-fluoroaniline
2-ethyl-6-bromoaniline
2-ethyl-6-methoxyaniline
2-ethyl-6-ethoxyaniline
2,6-diethylaniline
2-ethyl-6-propylaniline
2-ethyl-6-trifluoromethylaniline
2-propyl-6-chloroaniline
2-propyl-6-fluoroaniline
2-propyl-6-bromoaniline
2-propyl-6-methoxyaniline
2-propyl-6-ethoxyaniline
2,6-dipropylaniline
2-i-propyl-6-chloroaniline
2-i-propyl-6-fluoroaniline
2-i-propyl-6-methoxyaniline
2-butyl-6-chloroaniline
2-methyl-3-chloroaniline
2,4-dichloroaniline
2,5-dichloroaniline
2,6-dichloroaniline
2-chloro-3-methylaniline
2-chloro-4-methylaniline
2-chloro-5-methylaniline
2-chloro-5-fluoroaniline
2-chloro-5-bromoaniline
2-chloro-5-trifluoromethylaniline
2-fluoro-5-chloroaniline
2-chloro-6-fluoroaniline
2,6-methylaniline
2-methylaniline
2-ethylaniline
2-propylaniline
4-trifluoromethoxyaniline
4-methylsulfonylaniline
4-trifluoromethylaniline
3,4-dimethoxyaniline
3,4,5-trimethoxyaniline
3,4-diacetyloxyaniline
3,4-dibenzyloxyaniline
3,4,5-tribenzyloxyaniline
3,4-diethoxyaniline
2,4-dimethylaniline
2,4-diethylaniline
2-methyl-4-ethylaniline
2-ethyl-4-methylaniline
2-methyl-4-chloroaniline
2-methyl-4-bromoaniline
2-methyl-4-fluoroaniline
2-ethyl-4-chloroaniline
2-ethyl-4-fluoroaniline
2-methyl-4-methoxyaniline
2,4,6-trimethylaniline
2,4-dimethyl-6-ethylaniline
2,4-dimethyl-6-chloroaniline
2,4-dimethyl-6-bromoaniline
2,4-dimethyl-6-fluoroaniline
2,4-dimethyl-6-trifluoromethylaniline
2,4-dimethyl-6-nitroaniline
2,4-dimethyl-6-methoxyaniline
2,6-dimethyl-6-ethylaniline
2,6-dimethyl-4-chloroaniline
2,6-dimethyl-4-bromoaniline
2,6-dimethyl-4-fluoroaniline
2,6-dimethyl-4-methoxyaniline
2-methyl-4,6-dichloroaniline
2-methyl-4,6-difluoroaniline
2-methyl-4-fluoro-6-bromoaniline
2-methyl-4-methoxy-6-chloroaniline
2-methyl-4-ethyl-6-chloroaniline
2-methyl-4-chloro-6-trifluoromethylaniline
2-methyl-4-trifluoromethyl-6-chloroaniline
2-ethyl-4,6-dichloroaniline
2-ethyl-4,6-difluoroaniline
2-ethyl-4-fluoro-6-bromoaniline
2-ethyl-4-fluoro-6-chloroaniline
2-ethyl-4-bromo-6-chloroaniline
2-ethyl-4-chloro-6-fluoroaniline
2-ethyl-4-chloro-6-bromoaniline
2,6-diethyl-4-chloroaniline
2,6-diethyl-4-bromoaniline
2,6-diethyl-4-fluoroaniline
2,4-dimethyl-6-nitroaniline Table III 1-amidino-3-(2-methyl-6-chlorophenyl)thiourea
1-amidino-3-(2-methyl-6-fluorophenyl)thiourea
1-amidino-3-(2-methyl-6-bromophenyl)thiourea
1-amidino-3-(2-methyl-6-iodophenyl)thiourea
1-amidino-3-(2-methyl-6-methoxyphenyl)thiourea
1-amidino-3-(2-methyl-6-ethoxyphenyl)thiourea
1-amidino-3-(2-methyl-6-ethylphenyl)thiourea
1-amidino-3-(2-methyl-6-propylphenyl)thiourea
1-amidino-3-(2-methyl-6-butylphenyl)thiourea
1-amidino-3-(2-methyl-6-cyanophenyl)thiourea
1-amidino-3-(2-methyl-6-trifluoromethylphenyl)thiourea
1-amidino-3-(2-methyl-6-nitrophenyl)thiourea
1-amidino-3-(2-methyl-6-methylsulfonylphenyl)thiourea
1-amidino-3-(2-ethyl-6-chlorophenyl)thiourea
1-amidino-3-(2-ethyl-6-fluorophenyl)thiourea
1-amidino-3-(2-ethyl-6-bromophenyl)thiourea
1-amidino-3-(2-ethyl-6-methoxyphenyl)thiourea
1-amidino-3-(2-ethyl-6-ethoxyphenyl)thiourea
1-amidino-3-(2,6-diethylphenyl)thiourea
1-amidino-3-(2-ethyl-6-propylphenyl)thiourea
1-amidino-3-(2-ethyl-6-trifluoromethylphenyl)thiourea
1-amidino-3-(2-propyl-6-chlorophenyl)thiourea
1-amidino-3-(2-propyl-6-fluorophenyl)thiourea
1-amidino-3-(2-propyl-6-bromophenyl)thiourea
1-amidino-3-(2-propyl-6-methoxyphenyl)thiourea
1-amidino-3-(2-propyl-6-ethoxyphenyl)thiourea
1-amidino-3-(2,6-dipropylphenyl)thiourea
1-amidino-3-(2-i-propyl-6-chlorophenyl)thiourea
1-amidino-3-(2-i-propyl-6-fluorophenyl)thiourea
1-amidino-3-(2-i-propyl-6-methoxyphenyl)thiourea
1-amidino-3-(2-butyl-6-chlorophenyl)thiourea
1-amidino-3-(2-methyl-3-chlorophenyl)thiourea
1-amidino-3-(2-methyl-5-chlorophenyl)thiourea
1-amidino-3-(2,4-dichlorophenyl)thiourea
1-amidino-3-(2,5-dichlorophenyl)thiourea
1-amidino-3-(2,6-dichlorophenyl)thiourea
1-amidino-3-(2-chloro-3-methylphenyl)thiourea
1-amidino-3-(2-chloro-4-methylphenyl)thiourea
1-amidino-3-(2-chloro-5-methylphenyl)thiourea
1-amidino-3-(2-chloro-5-fluorophenyl)thiourea
1-amidino-3-(2-chloro-5-bromophenyl)thiourea
1-amidino-3-(2-chloro-5-trifluoromethylphenyl)thiourea 1-amidino-3-(2-chloro-5-chlorophenyl)thiourea
1-amidino-3-(2-chloro-6-fluorophenyl)thiourea
1-amidino-3-(2,6-difluorophenyl)thiourea
1-amidino-3-(2-methylphenyl)thiourea
1-amidino-3-(2-ethylphenyl)thiourea
1-amidino-3-(2-propylphenyl)thiourea
1-amidino-3-(4-trifluoromethoxyphenyl)thiourea
1-amidino-3-(4-trifluoromethylphenyl)thiourea
1-amidino-3-(4-methylsulfonylphenyl)thiourea
1-amidino-3-(3,4-dimethoxyphenyl)thiourea
1-amidino-3-(3,4,5-trimethoxyphenyl)thiourea
1-amidino-3-(3,4-acetyloxyphenyl)thiourea
1-amidino-3-(3,4-dibenzyloxyphenyl)thiourea
1-amidino-3-(3,4,5-tribenzyloxyphenyl)thiourea
1-amidino-3-(3,4-diethoxyphenyl)thiourea
1-amidino-3-(2,4-dimethylphenyl)thiourea
1-amidino-3-(2,4-diethylphenyl)thiourea
1-amidino-3-(2-methyl-4-ethylphenyl)thiourea
1-amidino-3-(2-ethyl-4-methylphenyl)thiourea
1-amidino-3-(2-methyl-4-chlorophenyl)thiourea
1-amidino-3-(2-methyl-4-bromophenyl)thiourea
1-amidino-3-(2-methyl-4-fluorophenyl)thiourea
1-amidino-3-(2-ethyl-4-chlorophenyl)thiourea
1-amidino-3-(2-ethyl-4-fluorophenyl)thiourea
1-amidino-3-(2-methyl-4-methoxyphenyl)thiourea
1-amidino-3-(2-ethyl-4-methoxyphenyl)thiourea
1-amidino-3-(2,4,6-trimethylphenyl)thiourea
1-amidino-3-(2,4-dimethyl-6-ethylphenyl)thiourea
1-amidino-3-(2,4-dimethyl-6-chlorophenyl)thiourea
1-amidino-3-(2,4-dimethyl-6-bromophenyl)thiourea
1-amidino-3-(2,4-dimethyl-6-fluorophenyl)thiourea
1-amidino-3-(2,4-dimethyl-6-trifluoromethyophenyl)thiourea
1-amidino-3-(2,4-dimethyl-6-nitrophenyl)thiourea
1-amidino-3-(2,4-dimethyl-6-methoxyphenyl)thiourea
1-amidino-3-(2,6-dimethyl-4-ethylphenyl)thiourea
1-amidino-3-(2,6-dimethyl-4-chlorophenyl)thiourea
1-amidino-3-(2,6-dimethyl-4-bromophenyl)thiourea
1-amidino-3-(2,4-dimethyl-6-fluorophenyl)thiourea
1-amidino-3-(2,4-dimethyl-6-trifluoromethylphenyl)thiourea
1-amidino-3-(2,4-dimethyl-6-nitrophenyl)thiourea
1-amidino-3-(2,4-dimethyl-6-methoxyphenyl)thiourea
1-amidino-3-(2,4-dimethyl-4-ethylphenyl)thiourea
1-amidino-3-(2,6-dimethyl-4-chlorophenyl)thiourea
1-amidino-3-(2,6-dimethyl-4-bromophenyl)thiourea
1-amidino-3-(2,6-dimethyl-4-fluorophenyl)thiourea
1-amidino-3-(2,6-dimethyl-4-methoxyphenyl)thiourea
1-amidino-3-(2-methyl-4,6-dichlorophenyl)thiourea
1-amidino-3-(2-methyl-4,6-difluorophenyl)thiourea
1-amidino-3-(2-methyl-4-fluoro-6-bromophenyl)thiourea
1-amidino-3-(2-methyl-4-fluoro-6-chlorophenyl)thiourea
1-amidino-3-(2-methyl-4-bromo-6-chlorophenyl)thiourea
1-amidino-3-(2-methyl-4-chloro-6-fluorophenyl)thiourea
1-amidino-3-(2-methyl-4-chloro-6-bromophenyl)thiourea
1-amidino-3-(2-methyl-4-methoxy-6-chlorophenyl)thiourea
1-amidino-3-(2-methyl-4-ethyl-6-chlorophenyl)thiourea
1-amidino-3-(2-methyl-4-chloro-6-trifluoromethylphenyl)thiourea
1-amidino-3-(2-methyl-4-trifluoromethyl-6-chlorophenyl)thiourea
1-amidino-3-(2-ethyl-4,6-dichlorophenyl)thiourea
1-amidino-3-(2-ethyl-4,6-difluorophenyl)thiourea
1-amidino-3-(2-ethyl-4-fluoro-6-bromophenyl)thiourea
1-amidino-3-(2-ethyl-4-fluoro-6-chlorophenyl)thiourea
1-amidino-3-(2-ethyl-4-bromo-6-chlorophenyl)thiourea
1-amidino-3-(2-ethyl-4-chloro-6-fluorophenyl)thiourea
1-amidino-3-(2-ethyl-4-chloro-6-bromophenyl)thiourea
1-amidino-3-(2,6-diethyl-4-chlorophenyl)thiourea
1-amidino-3-(2,6-diethyl-4-bromophenyl)thiourea
1-amidino-3-(2,6-diethyl-4-fluorophenyl)thiourea
1-amidino-3-(2,4-dimethyl-6-nitrophenyl)thiourea Hydrogenation of the 1-amidino-3-(3,4-diacetyloxyphenyl)thiourea and 1-amidino-3-(3,4-dibenzyloxyphenyl)thiourea with Pd/C in ethanol results in 1-amidino-3-(3,4-dihydroxyphenyl)thiourea. Hydrogenation of 1-amidino-3-(3,4,5-tribenzyloxyphenyl)thiourea with Pd/C in ethanol results in 1-amidino-3-(3,4,5-trihydroxyphenyl)thiourea.

Table IV presents representative amidinothioureas of the first type, e.g.:

$$\underset{H}{R_1-N-\overset{S}{\underset{\|}{C}}-N-\overset{NH}{\underset{\|}{C}}-N-R_4}$$

TABLE IV $$\underset{H}{R_1-N-\overset{S}{\underset{\|}{C}}-NH-\overset{NH}{\underset{\|}{C}}-N-R_4}$$

| $R_1$ | $R_4$ |
|---|---|
| 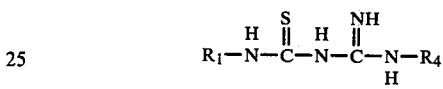 | CH$_3$ |
| 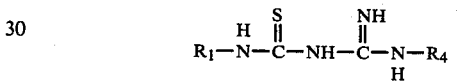 | 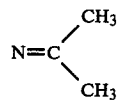 |
| 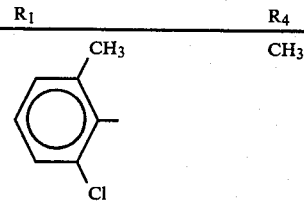 | H |
| 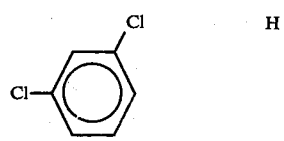 | H |
| 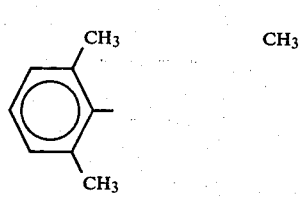 | CH$_3$ |

TABLE IV-continued $$R_1-\overset{H}{N}-\overset{\overset{S}{\|}}{C}-NH-\overset{\overset{NH}{\|}}{C}-\overset{}{N}-R_4$$
$$\phantom{R_1-N-C-NH-C-}H$$

| $R_1$ | $R_4$ |
|---|---|
| 4-Cl, 2-CH₃-phenyl | H |
| 2,6-diethylphenyl | H |
| 2,6-diethylphenyl | CH₃ |
| 4-Br, 2-Cl-phenyl | H |
| 4-Br, 2-Cl-phenyl | N=C(CH₃)₂ |
| 2,6-dichlorophenyl | H |
| 2,6-dichlorophenyl | N=C(CH₃)₂ |
| 4-Br, 2-CH₃-phenyl | H |

Table V presents representative amidinothioureas of the second type.

TABLE V $$R_1-\overset{H}{N}-\overset{\overset{NH}{\|}}{C}-NH-\overset{\overset{S}{\|}}{C}-\overset{}{N}-R_4$$
$$\phantom{R_1-N-C-NH-C-}H$$

| $R_1$ | $R_4$ |
|---|---|
| 4-Br, 2-CH₃-phenyl | H |
| 2,4-dichlorophenyl | H |
| 2,6-dimethylphenyl | C(CH₃)₃ |
| 2,6-dimethylphenyl | H |

Other Type I amidinothiourea compounds according to the present invention are listed in Table VI.

Table VI 1-(2',6'-diethylphenyl)-3-methylamidinothiourea
1-(2',6'-diethylphenyl)-3-ethylamidinothiourea
1-(2',6'-diethylphenyl)-3-i-propylamidinothiourea
1-(2',6'-diethylphenyl)-3-pentylamidinothiourea
1-(2',6'-diethylphenyl)-3-allylamidinothiourea
1-(2',6'-diethylphenyl)-3-propargylamidinothiourea
1-(2',6'-diethylphenyl)-3-cyclopropylamidinothiourea
1-(2',6'-diethylphenyl)-3-methoxyethylamidinothiourea
1-(2',6'-diethylphenyl)-3-benzyloxyethylamidinothiourea
1-(2',6'-diethylphenyl)-3-phenethoxyethylamidinothiourea
1-(2',6'-diethylphenyl)-3-benzylamidinothiourea
1-(2',6'-diethylphenyl)-3-(N,N-dimethylamidinothiourea
1-(2',6'-diethylphenyl)-3-(N,N-tetramethyleneamidinothiourea
1-(2'-methyl-6'-ethylphenyl)-3-methylamidinothiourea
1-(2'-methyl-6'-ethylphenyl)-3-t-butylamidinothiourea
1-(2'-methyl-6'-ethylphenyl)-3-propargylamidinothiourea
1-(2'-methyl-6'-ethylphenyl)-3-cyclopropylamidinothiourea
1-(2'-methyl-6'-ethylphenyl)-3-]N-(3'-cyclopentenyl)amidino]thiourea
1-(2'-methyl-6'-ethylphenyl)-3-phenethoxyethylamidinothiourea
1-(2'-methyl-6'-ethylphenyl)-3-benzylamidinothiourea
1-(2'-methyl-6'-ethylphenyl)-3-(N,N-diethylamidino)thiourea 1-(2'-methyl-6'-ethylphenyl)-3-[N,N(3'-methyl-3'-azapentamethylene)amidino]thiourea
1-(2'-methyl-6'-ethylphenyl)-3-[N,N-(3'-oxapentamethylene)amidino]thiourea
1-(2'-methyl-6'-chlorophenyl)-3-methylamidinothiourea
1-(2'-methyl-6'-chlorophenyl)-3-ethylamidinothiourea
1-(2'-methyl-6'-chlorophenyl)-3-propargylamidinothiourea
1-(2'-methyl-6'-chlorophenyl)-3-cyclohexylamidinothiourea
1-(2'-methyl-6'-chlorophenyl)-3-benzylamidinothiourea
1-(2'-methyl-6'-chlorophenyl)-3-methoxyethylamidinothiourea
1-(2'-methyl-6'-chlorophenyl)-3-(N,N-diethylamidinothiourea
1-(2'-methyl-6'-chlorophenyl)-3-(N,N-pentamethyleneamidinothiourea
1-(2'-methyl-6'-bromophenyl)-3-ethylamidinothiourea
1-(2'-ethyl-6'-chlorophenyl)-3-methylamidinothiourea
1-(2'-ethyl-6'-chlorophenyl)-3-benzyloxyethylamidinothiourea
1-(2'-ethyl-6'-fluorophenyl)-3-methylamidinothiourea
1-(2',6'-dimethyl-4'-hydroxyphenyl)-3-methylamidinothiourea
1-(2',6'-diethyl-4'-hydroxyphenyl)-3-methylamidinothiourea
1-(2'-methyl-6'-chloro-4'-hydroxyphenyl)-3-methylamidinothiourea
1-(2',6'-dimethyl-4'-aminophenyl)-3-methylamidinothiourea
1-(2',6'-diethyl-4'-aminophenyl)-3-methylamidinothiourea
1-(2',6'-dimethyl-4'-acetylaminophenyl)-3-methylamidinothiourea
1-(2'-methyl-6'-chloro-4-4'-acetylaminophenyl)-3-methylamidinothiourea
1-(2',6'-diethyl-4'-nitrophenyl)-3-methylamidinothiourea hydrochloride
1-(2',6'-diethyl-4'-aminophenyl)-3-methylamidinothiourea hydrochloride
1-(2',6'-dimethylphenyl)-3-(N,N-diethylamidino)thiourea hydrochloride
1-(2',6'-dimethylphenyl)-3-(N,N-propylamidino)thiourea hydrochloride
1-(2',6'-dimethylphenyl)-3-(N-methyl-N-benzyloxyethylamidino)thiourea hydrochloride
1-(2',6'-dimethylphenyl)-3-(N,N-tetramethyleneamidino)thiourea hydrochloride
1-(2',6'-dimethylphenyl)-3-(N-methylamidino)thiourea
1-(2',6'-dimethylphenyl)-3-(N,N-dimethylamidino)thiourea
1-(2',4',6'-trimethylphenyl)-3-(N-methylamidino)thiourea
1-(2',5'-dichlorophenyl)-3-(N-methylamidino)thiourea
1-(2',4',6'-triethylphenyl)-3-(N-methylamidino)thiourea
1-(2'-ethylphenyl)-3-(N-methylamidino)thiourea
1-(2',6'-dimethylphenyl)-3-(n-ethylamidino)thiourea
1-(2',6'-dimethylphenyl)-3-(N-propylamidino)thiourea
1-(2',6'-dimethylphenyl)-3-(N-i-propylamidino)thiourea
1-(2',6'-dimethylphenyl)-3-(N-t-butylamidino)thiourea
1-(2',6'-dimethylphenyl)-3-(N-cyclohexylamidino)thiourea
1-(2',6'-dimethylphenyl)-3-(N-phenylamidino)thiourea
1-(2',6'-dimethylphenyl)-3-(N-benzylamidino)thiourea
1-(2',6'-dipropylphenyl)-3-amidinothiourea
1-(2',6'-difluorophenyl)-3-amidinothiourea
1-(2',-propylphenyl)-3-amidinothiourea
1-(4',-trifluoromethylphenyl)-3-amidinothiourea
1-(2',6'-dimethylphenyl)-3-amidinothiourea
1-(2',6'-diethylphenyl)-3-amidinothiourea
1-(2'-methylphenyl)-3-amidinothiourea
1-(2'-methyl-6'-ethylphenyl)-3-amidinothiourea
1-(2',4',6'-trimethylphenyl)-3-amidinothiourea
1-(2',6'-dimethylphenyl)-3-[N-(2',6'-dimethylphenyl)amidino]thiourea Type II amidinothiourea compounds according to the present invention are listed in Table VII.

Table VII 1-methyl-3-(2',6'-diethylphenylamidino)thiourea
1-ethyl-3-(2',6'-diethylphenylamidino)thiourea
1-i-propyl-3-(2',6'-diethylphenylamidino)thiourea
1-pentyl-3-(2',6'-diethylphenylamidino)thiourea
1-allyl-3-(2',6'-diethylphenylamidino)thiourea
1-propargyl-3-(2',6'-diethylphenylamidino)thiourea
1-cyclopropyl-3-(2',6'-diethylphenylamidino)thiourea
1-phenyl-3-(2',6'-diethylphenylamidino)thiourea
1-methoxyethyl-3-(2',6'-diethylphenylamidino)thiourea
1-benzyloxyethyl-3-(2',6'-diethylphenylamidino)thiourea
1-phenethoxyethyl-3-(2',6'-diethylphenylamidino)thiourea
1-benzyl-3-(2',6'-diethylphenylamidino)thiourea
1-N,N'-dimethyl-3-(2',6'-diethylphenylamidino)thiourea
1-N,N'-tetramethylene-3-(2',6'-diethylphenylamidino)thiourea
1-cyclohexyl-3-(2',6'-diethylphenylamidino)thiourea
1-methyl-3-(2',6'-dimethylphenylamidino)thiourea
1-ethyl-3-(2',6'-dimethylphenylamidino)thiourea
1-i-propyl-3-(2',6'-dimethylphenylamidino)thiourea
1-pentyl-3-(2',6'-dimethylphenylamidino)thiourea
1-allyl-3-(2',6'-dimethylphenylamidino)thiourea
1-propargyl-3-(2',6'-dimethylphenylamidino)thiourea
1-cyclopropyl-3-(2',6'-dimethylphenylamidino)thiourea
1-phenyl-3-(2',6'-dimethylphenylamidino)thiourea
1-methoxyethyl-3-(2',6'-dimethylphenylamidino)thiourea
1-benzyloxyethyl-3-(2',6'-dimethylphenylamidino)thiourea
1-phenethoxyethyl-3-(2',6'-dimethylphenylamidino)thiourea
1-benzyl-3-(2',6'-dimethylphenylamidino)thiourea
1-N,N-dimethyl-3-(2',6'-dimethylphenylamidino)thiourea
1-N,N'-tetramethylene-3-(2',6'-dimethylphenylamidino)thiourea
1-cyclohexyl-3-(2',6'-dimethylphenylamidino)thiourea
1-methyl-3-(2',6'-diethylphenylamidino)thiourea
1-t-butyl-3-(2',6'-diethylphenylamidino)thiourea
1-propargyl-3-(2',6'-diethylphenylamidino)thiourea
1-cyclopropyl-3-(2'-methyl-6'-ethylphenylamidino)thiourea
1-N-(3'-cyclopentenyl)-3-(2'-methyl-6'-ethylphenylamidino)thiourea
1-phenethoxyethyl-3-(2'-methyl-6'-ethylphenylamidino)thiourea
1-benzyl-3-(2'-methyl-6'-ethylphenylamidino)thiourea
1-(N,N'-diethyl-3-(2'-methyl-6'-ethylphenylamidino)-thiourea
1-(N,N'(3'-methyl-3'-azapentamethylene)-3-(2'-methyl-6'-ethylphenylamidino)thiourea
1-(N,N'(3'-oxapentamethylene)-3-(2'-methyl-6'-ethylphenylamidino)thiourea 1-methyl-3-(2'-methyl-6'-chlorophenylamidino)thiourea
1-ethyl-3-(2'-methyl-6'-chlorophenylamidino)thiourea
1-propargyl-3-(2'-methyl-6'-chlorophenylamidino)thiourea
1-cyclohexyl-3-(2'-methyl-6'-chlorophenylamidino)thiourea
1-benzyl-3-(2'-methyl-6'-chlorophenylamidino)thiourea
1-methoxyethyl-3-(2'-methyl-6'-chlorophenylamidino)thiourea
1-(N,N'-diethyl)-3-(2'-methyl-6'-chlorophenylamidino)thiourea
1-(N,N'-pentamethylene)-3-(2'-methyl-6'-chlorophenylamidino)thiourea
1-ethyl-3-(2'-methyl-6'-bromophenylamidino)thiourea
1-methyl-3-(2'-ethyl-6'-chlorophenylamidino)thiourea
1-benzyloxy-3-(2'-ethyl-6'-chlorophenylamidino)thiourea
1-methyl-3-(2'-methyl-6'-fluorophenylamidino)thiourea
1-methyl-3-(2',6'-dimethyl-4'-hydroxyphenylamidino)thiourea
1-methyl-3-(2',6'-diethyl-4'-hydroxyphenylamidino)thiourea
1-methyl-3-(2'-methyl-6'-chloro-4'-hydroxyphenylamidino)thiourea
1-methyl-3-(2'-propylphenylamidino)thiourea
4'-trifluoromethylphenylamidinothiourea
2',6'-dimethyl-4'-chlorophenylamidinothiourea
2',6'-dimethylphenylamidinothiourea
2',6'-diethylphenylamidinothiourea
2'-methylphenylamidinothiourea
2'-methyl-6'-ethylphenylamidinothiourea
2',4',6'-trimethylphenylamidinothiourea
1-methyl-3-(2',6'-dimethyl-4'-aminophenylamidino)thiourea
1-methyl-3-(2',6'-diethyl-4'-aminophenylamidino)thiourea
1-methyl-3-(2',6'-dimethyl-4'-acetylaminophenylamidino)thiourea
1-methyl-3-(2',6'-methyl-6'-chloro-4'-acetylaminophenylamidino)thiourea
1-methyl-3-(2',6'-diethyl-4'-nitrophenylamidino)thiourea
1-methyl-3-(2',6'-dimethyl-4'-aminophenylamidino)thiourea
1-(N,N'-diethyl)-3-(2',6'-dimethylphenylamidino)thiourea
1-(N,N'-dipropyl)-3-(2',6'-dimethylphenylamidino)thiourea
1-(N-methyl-N-benzyloxyethyl)-3-(2',6'-dimethylphenylamidino)thiourea
1-(N,N-tetramethylene)-3-(2',6'-dimethylphenylamidino)thiourea
1-(N,N'-dimethyl)-3-(2',6'-dimethylphenylamidino)thiourea
1-methyl-3-(2',4',6'-trimethylphenylamidino)thiourea.

We claim:
1. A compound of the formula

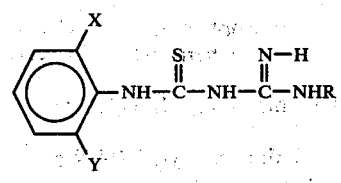

wherein
X and Y may be the same or different and are halo or lower alkyl;
R is lower alkynyl;
or a non-toxic salt thereof.

2. 1-(2,6-Diethylphenyl)-3-(propargylamidino) thiourea or a non-toxic salt thereof.

3. 1-(2-Ethyl-6-methylphenyl)-3-(propargylamidino) thiourea or a non-toxic salt thereof.

4. 1-(2-Chloro-6-methylphenyl)-3-(propargylamidino) thiourea or a nontoxic salt thereof.

5.

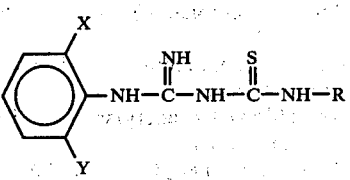

wherein
X and Y may be the same or different and are halo or lower alkyl;
R is lower alkynyl;
or a non-toxic salt thereof.

6. 1-Propargyl-3-(2,6-diethylphenylamidino) thiourea or a non-toxic salt thereof.

7. 1-Propargyl-3-(2,6-dimethylphenylamidino) thiourea or a non-toxic salt thereof.

8. 1-Propargyl-3-(2-ethyl,6-methylphenylamidino) thiourea or a non-toxic salt thereof.

9. 1-Propargyl-3-(2-chloro-6-methylphenylamidino) thiourea or a non-toxic salt thereof.

* * * * *

UNITED STATES PATENT AND TRADEMARK OFFICE
CERTIFICATE OF CORRECTION

PATENT NO. : 4,418,209

DATED : November 29, 1983

INVENTOR(S) : George H. Douglas et al.

Page 1 of 2

It is certified that error appears in the above-identified patent and that said Letters Patent is hereby corrected as shown below:

| | |
|---|---|
| Col. 3, line 18 | "pertain" should read --pertains--. |
| Col. 6, line 35 | Delete "$R_a$, $R_e$-loweralkyl, alkoxy substitution;". |
| Col. 7, line 16 | "cycloakyl" should read --cycloalkyl--. |
| Col. 8, line 68 | "incude" should read --include--. |
| Col. 10, line 35 | "Samdmeyer-type" should read --Sandmeyer-type--. |
| Col. 11, line 35 | "in" should read --is--. |
| Col. 13, line 49 | "is" should read --in--. |
| Col. 15, lines 50-51 | "dose,            3. Castor oil" should read --dose, p.3. Castor oil--. |
| Col. 18, line 40 | "diemthylsulfoxide" should read --dimethylsulfoxide--. |
| Col. 23, line 36 | "2,6-methylaniline" should read --2,6-difluoro-aniline--. |
| Col. 25, line 1 | "1-amidino-3-(2-chloro..." should read --1-amidino-3-(2,fluoro...--. |
| Col. 25, line 12 | "...(3,4-acetyl..." should read --...(3,4-diacetyl...--. |
| Col. 25, line 32 | "...6-trifluoromethyo..." should read --...6-trifluoromethyl...--. |
| Col. 28, line 62 | "...-3-]N-(3'-..." should read --...-3-[N-(3'-...--. |

UNITED STATES PATENT AND TRADEMARK OFFICE
CERTIFICATE OF CORRECTION

PATENT NO. : 4,418,209

DATED : November 29, 1983

INVENTOR(S) : George H. Douglas et al.

It is certified that error appears in the above-identified patent and that said Letters Patent is hereby corrected as shown below:

Col. 29, lines 17-18     "...pentamethyleneamidinothiourea" should read --...pentamethyleneamidino)thiourea--.

Col. 29, line 23     "1-(2'-ethyl-..." should read --1-(2'-methyl-...--.

Col. 29, line 40     "1-(2',6'-diethyl-..." should read --1-(2',6'-dimethyl-...--.

Col. 30, line 53     "1-methyl-3-(2'-6'-diethylphenylamidino)thiourea" should read --1-methyl-3-(2'-methyl-6'-ethylphenylamidino)thiourea--.

Col. 30, line 54     "1-t-butyl-3-(2',6'-diethylphenylamidino)thiourea" should read --1-t-butyl-3-(2'-methyl-6'-ethylphenylamidino)thiourea--.

Col 30, line 55     "1-propargyl-3-(2',6'-diethylphenylamidino)thiourea" should read --1-propargyl-3-(2'methyl-6'-ethylphenylamidino)thiourea--.

Signed and Sealed this

Eighteenth Day of December, 1990

Attest:

HARRY F. MANBECK, JR.

*Attesting Officer*     Commissioner of Patents and Trademarks